United States Patent [19]
Farer et al.

[11] Patent Number: 6,156,325
[45] Date of Patent: Dec. 5, 2000

[54] NAIL ENAMEL COMPOSITION CONTAINING A UREA-MODIFIED THIXOTROPIC AGENT

[75] Inventors: Alan Farer, Morganville; Chris Frankfurt, Old Bridge, both of N.J.

[73] Assignee: L'Oreal, Paris, France

[21] Appl. No.: 09/153,928

[22] Filed: Sep. 16, 1998

[51] Int. Cl.[7] .............................. A61K 6/00; A61K 7/00; A61K 7/04
[52] U.S. Cl. .............................. 424/401; 424/61
[58] Field of Search ...................... 424/401, 61

[56] References Cited

U.S. PATENT DOCUMENTS

| | | |
|---|---|---|
| 2,173,755 | 9/1939 | Fuller ........................ 167/85 |
| 3,438,796 | 4/1969 | Hanke ....................... 106/291 |
| 4,166,110 | 8/1979 | Isobe et al. ................ 424/61 |
| 4,179,304 | 12/1979 | Rossomando ............. 106/177 |
| 4,283,324 | 8/1981 | Duffy ....................... 260/31.2 N |
| 4,314,924 | 2/1982 | Haubennestel et al. .... 260/30.6 R |
| 4,410,570 | 10/1983 | Kreuzer et al. ........... 427/374.1 |
| 4,434,010 | 2/1984 | Ash .......................... 106/291 |
| 4,712,571 | 12/1987 | Remz et al. .............. 132/88.7 |
| 4,822,423 | 4/1989 | Soyama et al. ........... 106/5 |
| 4,838,648 | 6/1989 | Phillips et al. ........... 350/166 |
| 4,897,261 | 1/1990 | Yamazaki et al. ........ 424/61 |
| 4,930,866 | 6/1990 | Berning et al. ........... 350/320 |
| 4,954,619 | 9/1990 | Lang et al. ............... 536/20 |
| 5,071,639 | 12/1991 | Soyama et al. ........... 424/61 |
| 5,093,108 | 3/1992 | Pappas et al. ............ 424/61 |
| 5,130,125 | 7/1992 | Martin et al. ............. 424/61 |
| 5,145,671 | 9/1992 | Castrogiovanni et al. .. 424/61 |
| 5,171,363 | 12/1992 | Phillips et al. ........... 106/22 R |
| 5,174,996 | 12/1992 | Weber et al. ............. 424/401 |
| 5,364,467 | 11/1994 | Schmid et al. ........... 106/404 |
| 5,370,866 | 12/1994 | Frankfurt et al. ........ 424/61 |
| 5,569,535 | 10/1996 | Phillips et al. ........... 428/403 |
| 5,607,904 | 3/1997 | Jarrett ...................... 507/131 |
| 5,624,486 | 4/1997 | Schmid et al. ........... 106/404 |
| 5,658,976 | 8/1997 | Carpenter et al. ........ 524/403 |
| 5,688,494 | 11/1997 | Graves et al. ............ 424/61 |
| 5,725,866 | 3/1998 | Ramin ...................... 424/401 |
| 5,766,335 | 6/1998 | Bujard et al. ............. 106/404 |

FOREIGN PATENT DOCUMENTS

| | | |
|---|---|---|
| 0 395 410 | 10/1990 | European Pat. Off. . |
| WO 93/08237 | 4/1993 | WIPO . |

OTHER PUBLICATIONS

J. Pinsl et al., "Liquid Crystalline Polysiloxanes for Optical Write–Once Storage," *Journal of Molecular Electronics*, 3:9–13 (1987).

D. Makow, "Reflection and Transmission of Polymer Liquid–Crystal Coatings and Their Application to Decorative Arts and Stained Glass," National Research Council of Canada, 11:3 (1986).

"BYK Chemie Preliminary Data Sheet X4 for BYK®–410."

N. Haberle et al., "Right and Left Circular Polarizing Colorfilters Made From Crosslinkable Cholesteric LC–Silicones," Institution of Electrical Engineers, (1998).

Robert Maurer et al., "Polarizing Color Filters Made From Cholesteric LC Silicones," *SID 90 Digest*, (1990).

H.J. Eberle et al., "Inverse angle dependence of the reflection colours of cholesteric polymeric liquid crystals mixed with pigments," (1989).

M. Scholossman et al., "Advances in nail enamel technology," *J. Soc. Cosmet. Chem*, 43:331–337 (1992).

J. Hajas, "A Novel Liquid Rheology Additive for Solvent–Based and Solvent–Free Coatings," (1997).

*Primary Examiner*—Thurman K. Page
*Assistant Examiner*—S. Howard
*Attorney, Agent, or Firm*—Finnegan, Henderson, Farabow, Garrett & Dunner, L.L.P.

[57] ABSTRACT

A nail enamel composition which contains, in a cosmetically acceptable solvent, at least one film-forming substance and at least one urea-modified thixotropic agent. The use of such a thixotropic agent gives nail enamel compositions with higher gloss, high clarity, improved aesthetics in the bottle, excellent thixotropic properties, and improved application properties.

20 Claims, No Drawings

NAIL ENAMEL COMPOSITION CONTAINING A UREA-MODIFIED THIXOTROPIC AGENT

FIELD OF THE INVENTION

The present invention relates to a novel nail enamel composition with improved thixotropic properties as well as improved clarity in the bottle. More specifically, the invention relates to the use of a urea-modified compound as a thixotropic agent in a nail enamel composition.

BACKGROUND OF THE INVENTION

Various nail enamel compositions are known in the art. Nail enamel compositions typically contain, in an organic solvent or mixture of solvents, film-forming ingredients, plasticizing ingredients, and colorants. Generally, the composition also contains a thixotropic agent to thicken the composition in order to allow better spreading on the nail. The thixotropic agent also acts to suspend the colorant.

The classic thixotropic agent used in the prior art is a bentonite clay. Aromatic organic solvents in particular cause these clays to swell, thus providing a gel with good thixotropic properties, i.e., rendering the composition capable of passing from a gelled state to a liquid state simply by stirring and from liquid to gel after standing. A composition containing such a gel thus exhibits relatively good dispersion stability without sedimentation or separation over a long period. Further, such compositions do not require the vigorous shaking that other compositions often require after extended periods of storage.

The clay thixotropes, however, produce cloudy suspensions, rendering the composition opaque and often giving it a more or less yellowish color inside the bottle, unpleasant to the eye. Although this opacity is generally masked by the presence of colorants and/or pigments in the composition, the use of the clay thixotropes diminishes gloss in the final formulated nail enamel product. Thus the need remains for a thixotropic agent that will not affect the glossiness of the nail enamel and yet will have sufficient thixotropic properties such that the stability of the composition is not compromised.

SUMMARY OF THE INVENTION

In order to achieve these and other advantages, the present invention is drawn to a novel nail enamel composition containing, in a cosmetically acceptable solvent, at least one film-forming substance and at least one urea-modified thixotropic agent wherein the urea-modified thixotropic agent is a urea urethane having the following formula:

R—O—CO—NH—R'—NH—CO—NH—R"—NH—CO—NH—R'—NH—CO—OR wherein R represents $C_nH_{2n+1}$— or $C_mH_{2m+1}(C_pH_{2p}O)_r$—; n represents an integer having a value of from 4 to 22; m represents an integer having a value of from 1 to 18; p represents an integer having a value of from 2 to 4; and r represents an integer having a value of from 1 to 10.

R' represents:

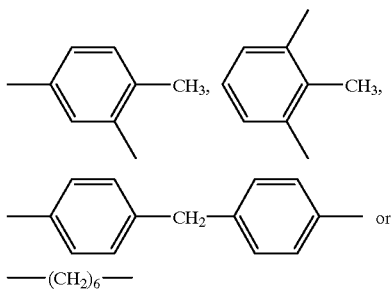

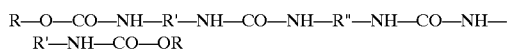

and R" represents:

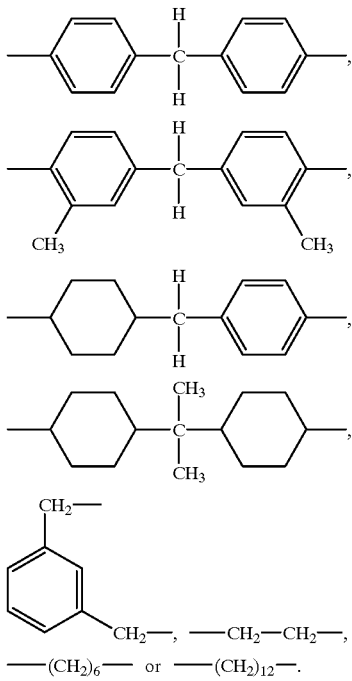

The nail enamel composition of the invention may also contain a plasticizer and optionally a coloring agent. The present inventors have discovered that the use of a urea-modified thixotropic agent in place of, or in conjunction with, the clay thixotropes of the prior art, results in a clear suspension with improved gloss. In general, nail enamel compositions containing clay thixotropes only are difficult to process because their creation requires a great deal of high shear. Also, since the clay thixotropes are naturally occurring products, they can vary in quality and consistency. In contrast, the presently claimed compositions utilizing the novel urea-modified thixotrope are easy to produce consistently at optimum conditions because their creation does not require high shear processing.

Reference will now be made in detail to the present preferred embodiment(s) of the invention.

DETAILED DESCRIPTION OF THE PREFERRED EMBODIMENTS

The presently claimed invention is drawn to a nail enamel composition which contains, in a cosmetically acceptable solvent, at least one film-forming substance and at least one urea-modified thixotropic agent. The present inventors have found that the use of such a thixotropic agent gives nail enamel compositions with higher gloss, high clarity, improved aesthetics in the bottle, excellent thixotropic properties, and improved application properties.

The urea-modified thixotropic agents used in the present invention are urea urethanes having the following formula:

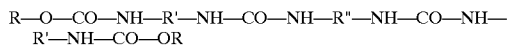

wherein R represents $C_nH_{2n+1}$— or $C_mH_{2m+1}(C_pH_{2p}O)_r$—; n represents an integer having a value of from 4 to 22; m represents an integer having a value of from 1 to 18; p represents an integer having a value of from 2 to 4; and r represents an integer having a value of from 1 to 10.

R' represents:

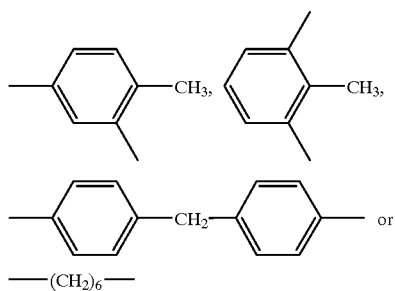

and R" represents:

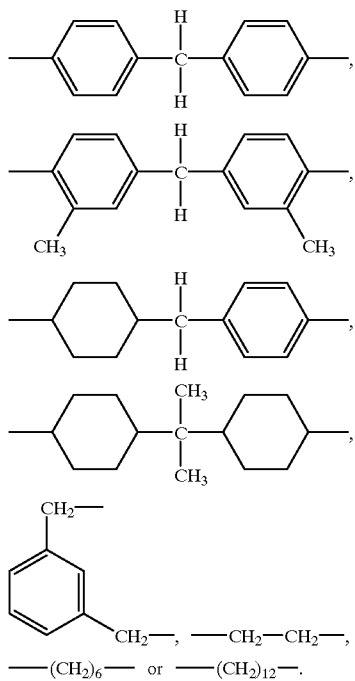

Such a urea-modified product can be purchased from BYK-Chemie in a dilute solution with N-methyl-pyrrolidone as solvent under the trade name of BYK®-410 and is generally described in U.S. Pat. No. 4,314,924. The at least one urea-modified thixotropic agent is preferably present in an amount of from about 0.05 to about 0.40% relative to the weight of the composition. More preferably, the at least one urea-modified thixotropic agent is present in an amount of from about 0.25 to about 0.35% relative to the weight of the composition.

The nail enamel composition of the invention may contain at least one additional thixotropic agent, used in conjunction with the at least one urea-modified agent. When such an additional thixotropic agent is present, the composition comprises from about 0.10 to about 0.30% of the at least one urea-modified thixotropic agent relative to the weight of the composition and up to about 1.0% of the additional thixotropic agent. The additional thixotropic agent(s) may be selected from conventional silica or bentonite clay agents. Particularly preferred is stearalkonium hectorite, sold by RHEOX as BENTONE 27.

Film forming substances useful in the present invention include, but are not limited to, conventional film-forming agents such as nitrocellulose, other cellulose derivatives, such as cellulose acetate, cellulose acetate butyrate, and ethyl cellulose; polyesters; resins, such as polyurethane resins, alkyd resins, and polyvinyl resins such as polyvinyl acetate, polyvinyl chloride, polyvinylbutyrate; (meth)acrylic and vinyl copolymers such as styrene/butadiene copolymers, acrylate/vinyl acetate copolymers, acrylonitrile/butadiene copolymers, and ethylene/vinyl acetate copolymers.

The primary film-forming agent is preferably nitrocellulose, which is known to give hardness and resistance to abrasion. If a second film-forming substance is present, this second film-forming substance is preferably selected from cellulose acetate butyrate, polyesters, polyurethanes, and acrylates. The film-forming substance is preferably present in an amount of from about 5% to about 20% by weight relative to the weight of the composition, and more preferably from about 10% to about 14%. Suitable modifiers for the primary film-forming agent include arylsulfonamide resins such as arylsulfonamide formaldehyde or epoxy resins.

The presently claimed composition preferably contains at least one plasticizer. Plasticizers useful in the presently claimed nail enamel composition include plasticizers commonly employed in nail varnish compositions. These plasticizers encompass, but are not limited to, dibutyl phthalate, dioctyl phthalate, tricresyl phthalate, butyl phthlate, dibutoxy ethyl phthalate, diamylphthalate, tosyl amide, N-ethyl-tosyl amide, sucrose acetate isobutyrate, camphor, castor oil, citrate esters, glyceryl diesters, glyceryl triesters, tributyl phosphate, tri-phenyl phosphate, butyl glycolate, benzyl benzoate, butyl acetyl ricinoleate, butyl stearate, and dibutyl tartrate. Particularly preferred as a plasticizer in the present invention is the mixture of acetyl tributyl citrate and N-ethyl tosyl amide. The plasticizer is preferably present in an amount of from about 3% to about 12% by weight relative to the weight of the composition.

The solvents useful in the present invention are cosmetically acceptable organic solvents including, but not limited to toluene, xylene, alkyl acetates such as ethyl acetate and butyl acetate; ketones such as acetone or methyl ethyl ketone; alkanes such as hexane or heptane; alkyl alcohols such as ethanol, isopropanol, and butanol; glycol ethers; N-methyl pyrrolidone; and alkyl lactates. A preferred solvent is alkyl acetate. The solvent or mixture of solvents is preferably present in an amount of from about 40% to about 80% by weight relative to the weight of the composition, and more preferably from about 65% to about 78%.

The nail enamel composition of the invention also preferably contains at least one coloring agent. Conventional coloring agents can be used, and preferred coloring agents include inorganic pigments such as titanium dioxide, iron oxides, titanated mica, iron oxide coated mica, ultramarine, chromium oxide, chromium hydroxide, manganese violet, bismuth oxychloride, guanine, and aluminum; pearlescent materials; and organic coloring agents such as ferric ammonium ferrocyanide, and D&C Red Nos. 6, 7, 34, Blue No. 1, Violet No. 2, and Yellow No. 5.

The inorganic pigments may be surface-treated as is customary to prevent migration or striation. Silicones and polyethylenes are most often used as the coatings for inorganic pigments and are preferred according to the present invention. Colorant materials may also include chips or powder of mica or diamonds in the nail composition. Also useful are specialty materials giving rise to two-tone color effects such as liquid crystal silicones or multi-lamellar metallic particulates, which generally can be mixed with pigments or dyes to obtain a broader spectrum of brilliant color and increased luminous reflectance. Such materials are described in, e.g., U.S. Pat. No. 3,438,796; U.S. Pat. No. 4,410,570; U.S. Pat. No. 4,434,010; U.S. Pat. No. 4,838,648; U.S. Pat. No. 4,930,866; U.S. Pat. No. 5,171,363; U.S. Pat. No. 5,364,467; U.S. Pat. No. 5,569,535; U.S. Pat. No. 5,607,904; U.S. Pat. No. 5,624,486; U.S. Pat. No. 5,658,976; U.S. Pat. No. 5,688,494; U.S. Pat. No. 5,766,335; N. H äberle et al., "Right and Left Circular Polarizing Colorfilters made from Crosslinkable Cholesteric LC-Silicones," Conference Record of the 1991 International Display Research Conference (IEEE), pp. 57–59; R. Maurer et al., "Polarizing Color Filters made from Cholesteric LC-Silicones," SID 90 Digest (1990), pp. 110–113; H.-J. Eberle et al., "Inverse Angle Dependence of the Reflection Colours of Cholesteric Polymeric Liquid Crystals Mixed with Pigments," Liquid Crystals, 5(3), (1989), pp. 907–916; J. Pinsl et al., "Liquid Crystalline Polysiloxanes for Optical Once-Write Storage," J. Molec. Electr., Vol. 3 (1987), pp. 9–13; and D. Makow, "Reflection and Transmission of Polymer Liquid-Crystal Coatings and their Application to Decorative Arts and Stained Glass," Color Res. Applic. Vol. 11, No. 3, (1986), pp. 205–208, all of which are incorporated herein by reference in their entirety.

Preferably, the coloring agent is present in the nail enamel composition in an amount up to about 5% by weight relative to the total weight of the composition. More preferably, the coloring agent is present in an amount of from 2% to 3% by weight.

The composition according to the invention may also include additives recognized by a person skilled in the art as being capable of incorporation into such a composition. For example, the composition may include at least one cosmetically active compound, which may be selected from vitamins, minerals, moisturizers, hardening agents such as silica and formaldehyde/glyoxal, UV absorbers, and fibers such as nylon or aramide fibers. Any art-recognized UV absorber can be used, both organic and inorganic. Preferred inorganic UV absorbers include titanium dioxide and zinc oxide, both of which may be used in nanoparticulate form. Preferred organic UV absorbers include octocrylene, octylmethoxy cinnamate, and benzophenone.

Additional additive ingredients may include keratin and its derivatives, melanin, collagen, cystine, chitosan and its derivatives, ceramides, biotin, oligoelements, protein hydrolysates, and phospholipids.

A person skilled in the art can, without undue experimentation, select those optional additional compounds and/or their quantity, so that the advantageous properties of the composition according to the invention are not, or are not substantially, impaired by the inclusion of such additives.

The composition according to the invention may be prepared by a person skilled in the art on the basis of his or her general knowledge and according to the state of the art.

The composition according to the invention may be in the form of a product to be applied to the nails, such as a top coat, a base coat, or a pigmented nail lacquer or varnish.

The invention will be further clarified by the following examples, which are intended to be illustrative of the invention, but not limiting thereof.

EXAMPLE

Three compositions were formulated as set forth in the following table. The amounts listed are in grams.

| INGREDIENTS | COMPOSITION 1 | COMPOSITION 2 | COMPOSITION 3 |
| --- | --- | --- | --- |
| Ethyl Acetate | 25.65 | 21.00 | 23.65 |
| Butyl Acetate | 25.00 | 24.00 | 25.00 |
| Propyl Acetate | 20.00 | 15.00 | 20.00 |
| Nitrocellulose | 10.00 | 14.70 | 10.00 |
| Isopropyl Alcohol | 5.00 | 5.00 | 5.00 |
| Sucrose Acetate Isobutyrate | 5.00 | — | 5.00 |
| N-Ethyl Tosylamide | 5.00 | 7.50 | 5.00 |
| Tosylamide Epoxy Resin | 2.00 | 9.00 | 2.00 |
| Acrylates Copolymer | 1.50 | — | 1.50 |
| Stearalkonium Hectorite | — | 1.00 | — |
| Etocrylene | 0.50 | 0.50 | 0.50 |
| Benzophenone-1 | 0.10 | 0.10 | 0.10 |
| Colorants/Pearls | — | 2.00 | 2.00 |
| Modified Urea-Urethane (BYK 410) | 0.25 | 0.20 | 0.25 |

Each of compositions 1–3 were visually compared with a "classic" nail enamel composition, i.e., one containing only the traditional clay-based thixotrope. The comparisons are described below.

Composition 1, which was a formulation according to the invention but which contained no colorants, i.e., was a clear top coat enamel. This formulation exhibited significantly improved body and viscosity, while maintaining excellent clarity, when compared to the "classic" composition.

Composition 2 was similar to composition 1 but did not contain sucrose acetate isobutyrate, one of the plasticizers, or acrylates copolymer, one of the film-formers. Composition 2 did contain, however, pigments and pearlescent colorants and, in addition to the urea-urethane (BYK-410) as a thixotrope, contained a clay-based thixotrope, stearalkonium hectorite. The result was a pigmented/pearlescent nail enamel with no perceptible (visual) differences over the "classic" compositions.

Finally, composition 3 was an inventive pigmented/pearlescent nail enamel utilizing only the modified urea-urethane as the thixotrope. This product displayed improved bottle aesthetics (gloss) and a smoother finish on the nail versus a "classic" nail enamel which utilized the clay type thixotropes.

Overall, the inventive compositions had higher gloss; better stability, i.e., even with pigments that are normally difficult to suspend; and improved application properties, e.g., almost no brush marks were perceptible on the nail after the composition dried, when compared to the "classic" compositions.

It will be apparent to those skilled in the art that various modifications and variations can be made in the compositions of the invention without departing from the spirit or scope of the invention. Thus, it is intended that the present invention cover the modifications and variations of this invention provided that they come within the scope of the appended claims and their equivalents.

What is claimed is:

1. A nail enamel composition comprising, in a cosmetically acceptable solvent:
   at least one film-forming substance and
   at least one urea-modified thixotropic agent, wherein said at least one urea-modified thixotropic agent is a urea urethane having the following formula:

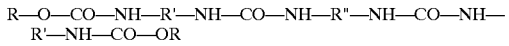

wherein:
   R represents $C_nH_{2n+1}-$ or $C_mH_{2m+1}(C_pH_{2p}O)_r-$;
   n represents an integer having a value of from 4 to 22;
   m represents an integer having a value of from 1 to 18;
   p represents an integer having a value of from 2 to 4;
   r represents an integer having a value of from 1 to 10;
   R' represents:

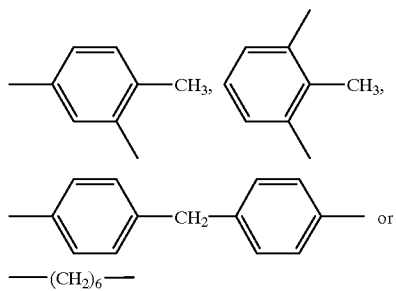

and R" represents:

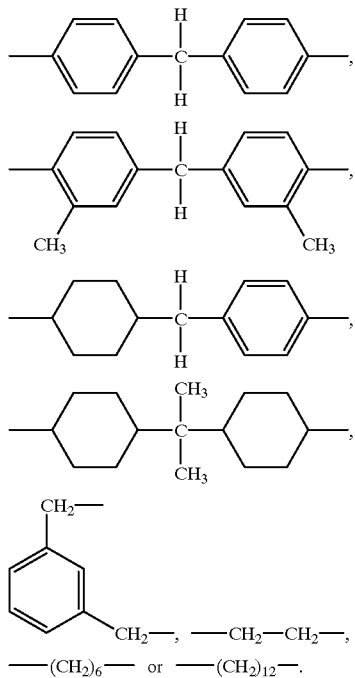

2. A nail enamel composition according to claim 1, said nail enamel composition further comprising at least one plasticizer.

3. A nail enamel composition according to claim 1, said nail enamel composition further comprising an additional film-forming substance.

4. A nail enamel composition according to claim 1, said nail enamel composition further comprising an additional thixotropic agent.

5. A nail enamel composition according to claim 1, said nail enamel composition further comprising at least one coloring agent.

6. A nail enamel composition according to claim 1, wherein said at least one film-forming substance is selected from nitrocellulose, other celluloses derivatives, resins, polyesters, and (meth)acrylic and vinyl copolymers.

7. A nail enamel composition according to claim 6, wherein said cellulose derivatives are selected from cellulose acetate, cellulose acetate butyrate, and ethyl cellulose, said resins are selected from alkyd resins, polyvinyl resins, and polyurethane resins, and said meth(acrylic and vinyl copolymers are selected from acrylonitrile/butadiene copolymers, styrene/butadiene copolymers, acrylate/vinyl acetate copolymers, and ethylene/vinyl acetate copolymers.

8. A nail enamel composition according to claim 7, wherein said polyvinyl resins are polyvinyl acetate, polyvinyl chloride, polyvinyl butyrate, or mixtures thereof.

9. A nail enamel composition according to claim 6, wherein said at least one film-forming substance is nitrocellulose.

10. A nail enamel composition according to claim 3, wherein said additional film-forming substance is cellulose acetate butyrate, a polyester, a polyurethane, an acrylate, or a mixture thereof.

11. A nail enamel composition according to claim 1, further comprising a modifier for said at least one film-forming substance, wherein said modifier is an arylsulfonamide resin.

12. A nail enamel composition according to claim 1, wherein said cosmetically acceptable solvent is an alkyl acetate, toluene, xylene, a ketone, an alkane, an alkyl alcohol, a glycol ether, N-methyl pyrrolidone, an alkyl lactate, or a mixture thereof.

13. A nail enamel composition according to claim 1, wherein said alkyl acetate is an ethyl acetate or butyl acetate, or a mixture thereof;
   said ketone is acetone or methyl ethyl ketone or a mixture thereof;
   said alkane is hexane or heptane or a mixture thereof; and
   said alkyl alcohol is ethanol, isopropanol, or butanol or a mixture thereof.

14. A nail enamel composition according to claim 2, wherein said at least one plasticizer is dibutyl phthalate, dioctyl phthalate, tricresyl phthalate, butyl phthlate, dibutoxy ethyl phthalate, diamylphthalate, tosyl amide, N-ethyltosylamide, sucrose acetate isobutyrate, camphor, castor oil, citrate ester, glyceryl diester, glyceryl triester, tri-phenyl phosphate, butyl glycolate, benzyl benzoate, tributyl phosphate, butyl acetyl ricinoleate, butyl stearate, and dibutyl tartrate or a mixture thereof.

15. A nail enamel composition according to claim 14, wherein said at least one plasticizer is a mixture of acetyl tributyl citrate and N-ethyl tosylamide.

16. A nail enamel composition according to claim 4, wherein said additional thixotropic agent is stearalkonium hectorite.

17. A nail enamel composition according to claim 1, wherein:

said cosmetically acceptable solvent is present in an amount of from about 40% to about 80% by weight relative to the weight of the composition, said at least one film-forming substance is present in an amount of from about 5% to about 20% by weight relative to the weight of the composition, said at least one plasticizer is present in an amount of from about 3% to about 12% by weight relative to the weight of the composition, and said at least one urea-modified thixotropic agent is present in an amount of from about 0.05 to about 0.40% relative to the weight of the composition.

18. A nail enamel composition according to claim 17, wherein said at least one urea-modified thixotropic agent is present in an amount of from about 0.25 to about 0.35% relative to the weight of the composition.

19. A nail enamel composition according to claim 17, wherein said nail enamel composition comprises from about 0.10 to about 0.30% of said at least one urea-modified thixotropic agent relative to the weight of the composition and up to about 1% of an additional thixotropic agent.

20. A nail enamel composition according to claim 1, wherein said nail enamel composition further comprises at least one cosmetically active compound selected from vitamins, minerals, moisturizers, hardening agents, UV absorbers and fibers.

* * * * *

UNITED STATES PATENT AND TRADEMARK OFFICE
CERTIFICATE OF CORRECTION

PATENT NO. : 6,156,325
DATED : December 5, 2000
INVENTOR(S) : Alan Farer et al.

Page 1 of 1

It is certified that error appears in the above-identified patent and that said Letters Patent is hereby corrected as shown below:

Claim 6, column 8,
Line 9, "celluloses derivatives" should read -- cellulose derivatives --.

Claim 13, column 8,
Line 41, "claim 1" should read -- claim 12 --.

Claim 14, column 8,
Line 51, "butyl phthlate" should read -- butyl phthalate --.

Signed and Sealed this

Twenty-fifth Day of September, 2001

Attest:

*Nicholas P. Godici*

NICHOLAS P. GODICI
*Attesting Officer*    *Acting Director of the United States Patent and Trademark Office*